US010008013B2

(12) United States Patent
Crnokrak

(10) Patent No.: US 10,008,013 B2
(45) Date of Patent: Jun. 26, 2018

(54) MULTIDIMENSIONAL HALO-BASED VISUALIZATION SYSTEM

(71) Applicant: ORA Inc., Los Angeles, CA (US)

(72) Inventor: Peter Crnokrak, London (GB)

(73) Assignee: ORA Inc., Los Angeles, CA (US)

(*) Notice: Subject to any disclaimer, the term of this patent is extended or adjusted under 35 U.S.C. 154(b) by 202 days.

(21) Appl. No.: 14/868,702

(22) Filed: Sep. 29, 2015

(65) Prior Publication Data

US 2016/0098847 A1   Apr. 7, 2016

Related U.S. Application Data

(60) Provisional application No. 62/058,642, filed on Oct. 1, 2014.

(51) Int. Cl.
| | |
|---|---|
| *G06T 11/20* | (2006.01) |
| *G06T 11/00* | (2006.01) |
| *G06T 11/60* | (2006.01) |
| *A61B 5/00* | (2006.01) |
| *A61B 5/0205* | (2006.01) |
| *A61B 5/11* | (2006.01) |

(52) U.S. Cl.
CPC ........ *G06T 11/203* (2013.01); *A61B 5/02055* (2013.01); *A61B 5/6898* (2013.01); *G06T 11/001* (2013.01); *G06T 11/60* (2013.01); *A61B 5/0015* (2013.01); *A61B 5/1102* (2013.01); *A61B 5/1112* (2013.01); *A61B 5/1118* (2013.01); *A61B 5/4812* (2013.01); *A61B 5/7475* (2013.01)

(58) Field of Classification Search
CPC .... G06T 11/203; G06T 11/206; A61B 5/1118; G06F 19/26
See application file for complete search history.

(56) References Cited

U.S. PATENT DOCUMENTS

| | | | | |
|---|---|---|---|---|
| 8,068,104 | B2* | 11/2011 | Rampersad | G06F 19/3406 345/419 |
| 9,480,435 | B2* | 11/2016 | Olsen | A61B 5/742 |
| 9,594,473 | B2* | 3/2017 | Lee | G06F 3/165 |
| 2016/0302717 | A1* | 10/2016 | Tawa | G06F 19/3481 |
| 2017/0132816 | A1* | 5/2017 | Aston | G06T 11/206 |

OTHER PUBLICATIONS

"Circle Audio Spectrum"—Render Forest. Circle audio spectrum template. https://www.renderforest.com/template/circle-audio-spectrum. Feb. 1, 2016. Render Forest discloses an audio spectrum template that displays audio frequencies in a ring/circle format.*

* cited by examiner

*Primary Examiner* — Antonio A Caschera
(74) *Attorney, Agent, or Firm* — Ascenda Law Group, PC

(57) ABSTRACT

Systems, methods, and machine readable media for visualizing complex data, including real-time data streams from wearable device sensors, may use a halo-based representation. Halos are comprised of multiple rings that can be used to efficiently convey, for example, information about the status of a subject, such as a subject's heart rate, activity level, and calories burned at particular times throughout a day.

20 Claims, 9 Drawing Sheets

MULTIDIMENSIONAL HALO-BASED VISUALIZATION SYSTEM

CROSS-REFERENCE TO RELATED APPLICATIONS

This application claims the benefit of U.S. Provisional Application No. 62/058,642, filed Oct. 1, 2014, which is incorporated by reference in its entirety.

FIELD OF THE INVENTION

The present invention relates to data management and visualization using a multidimensional halo-based system, where halos are comprised of rings, and halos may be compared to other halos.

BACKGROUND

Large data sets can be difficult to manage and analyze with because of limitations inherent in traditional approaches for viewing and analyzing data. For example, static charts and traditional databases typically do not provide interfaces for visualizing relationships between different records, much less visualizing relationships between large numbers of different records, and provide cumbersome and non-intuitive approaches for aggregating structured data.

Additionally, with the ongoing improvements in wearable devices that can generate multiple real-time data streams, there is a great need for new approaches for integrating wearable devices with systems for analyzing and making sense of multiple sensor feeds of data in real-time. Even for static, traditional data sets, it can be challenging for consumers and professionals to identify correlations between multiple categories of data, especially when communicated in a traditional manner using a series of bar charts.

There is a need for systems to handle large, structured datasets that can integrate data from multiple devices and sensors, and also enable visualization of relationships between the data. Disclosed herein are embodiments of an invention that address these needs.

DETAILED DESCRIPTION OF THE INVENTION

The present invention relates to data visualization using multiple dimensions. For example, the methods and associated systems described herein enable visualizing and interacting with data that is structured in time and space. Such a structure enables a user to intuitively and efficiently interact with and perceive relationships in the data, such as intrinsic correlations between different categories of data, such as health-related data. These features are unavailable in conventional representations for data, such as a corresponding series of two-dimensional graphs or bar charts. While the halo representation described here is a novel and unusual approach for data visualization, the generally circular shape can facilitate intuitive understanding through the use of visual metaphors such as successive rings indicating the passage of time like tree rings, or a pulsing halo mimicking a beating heart.

Additionally, the halo-based visualization and analysis of data as described here can identify natural thresholds in the complex data sets that, in the case of human health data, can improve diagnostics by professionals.

As used herein, a halo refers to a set of circular rings.

As used herein, "circular" means suggesting or forming a closed, generally circular shape. Such a shape may be suggested by, for example, dots or dashes organized into an annular arrangement. A circular shape may also incorporate local sinusoidal or jagged distortions, such as the distortions shown in the accompanying FIGS. 1-6, or other types of larger distortions that may animate between a distorted and generally circular shape, or an oval shape.

Figure 1:
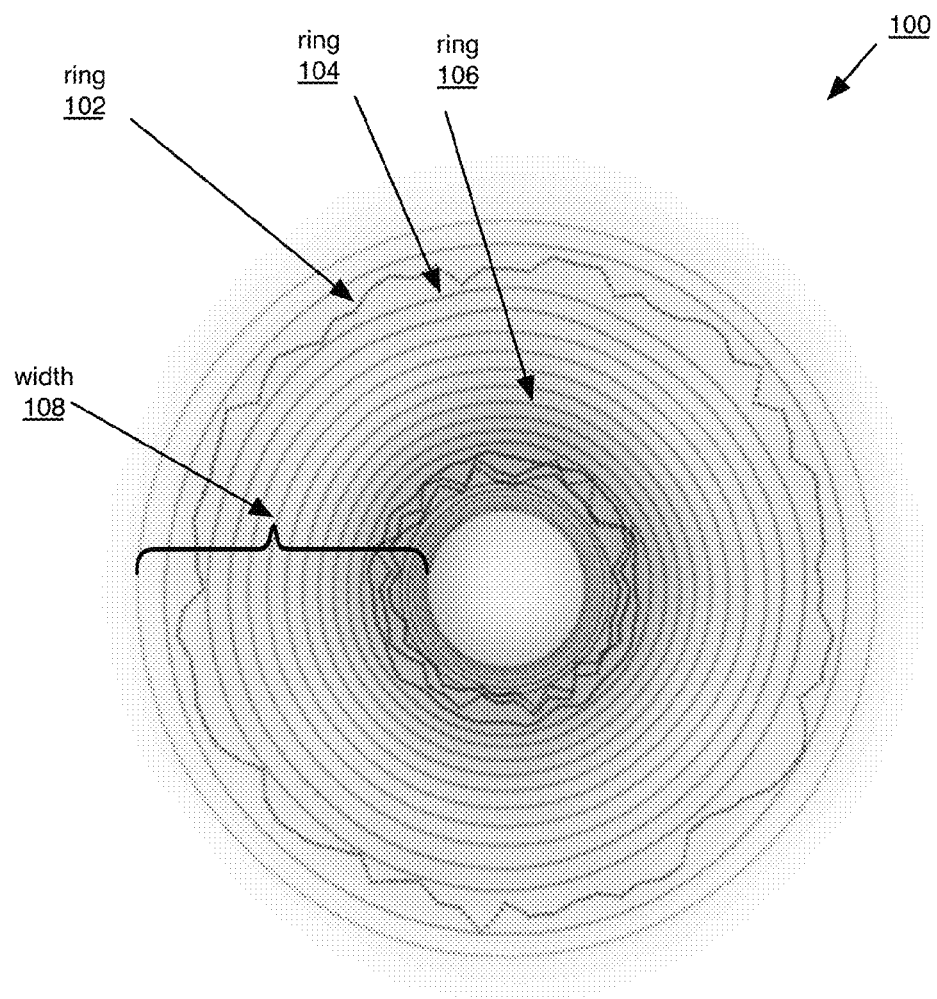
FIG. 1 shows one view of a halo, consistent with one embodiment of the invention.

FIG. 1 shows one view of an exemplary halo 100. A halo is an annular structure comprised of a set of rings. The rings as a group define the shape of the halo. For example, halo 100 is comprised of a set of rings including ring 102, ring 104, and ring 106.

A halo may be used to visualize complex data sets. For example, halo 100 may be used to visualize the physical activity and health of a person over the course of a day. In this particular example, each ring may represent the person's activity data for one hour. In this example, the innermost ring corresponds to measurements from the first hour of the day, and the outermost ring corresponds to measurements from the most recent hour of the day, with each intermediate ring corresponding to an hour of the day in sequence. In halo 100, the hour represented by ring 106 preceded the hours represented by rings 104 and 102. The color of each ring may indicate the number of calories burned during each hour. The complexity of each ring may indicate the level of physical activity during each hour, where the complexity refers to the magnitude and frequency of distortions in the ring. For example, in halo 100, ring 102 has a greater complexity compared to rings 104 and 106, indicating that the person was more active during the hour corresponding to ring 102 than during the hours corresponding to 104 and 106. The exemplary depiction of halo 100 in FIG. 1 provides an intuitive, graphical description indicating that the person was active for a few hours in the morning, then had a series of sedentary hours during the middle of the day, and then had another active hour toward the end of the day before two more sedentary hours.

In certain embodiments, the system includes a computing device that receives one or more data streams that are transformed into one or more halos. A data stream may be a sequence of data elements or data sets that become available to the computing device over time. In certain embodiments, the computing device receives one or more discrete data sets that are transformed into one or more halos. The received data represent information about the status of a subject. For example, the information may describe the physical status of a patient or consumer, strengths and attributes of a character in a game, changes in the values of a set of stock market listings, or weather conditions at a geographic location.

In certain embodiments, the data received by the computing device includes heart rate data, heat flux data, EKG waveforms, accelerometer data, altimeter data, gyroscope data, or GPS data. In certain embodiments, the data received may include blood alcohol data, blood oxygen data, temperature data, skin conductance data, ballistocardiogram data, blood pressure data, blood glucose data, or sound data. In certain embodiments, such data includes data for a character in a game such as the character's wins and losses, character attributes, and damage taken.

In certain embodiments, the data received by the computing device is transformed into a metric providing information about the status of a subject. Transformation may involve calculating a summary or average, or combining multiple types of data into a combined value. In certain embodiments, the data are already in the form of metrics for use in a halo. Metrics may include, for example, heart rate, distance travelled, elevation climbed, step count, standing duration, activity duration, speed of movement, intensity of movement, calories burned, sleep cycle, hydration, electrical skin conductance, tremor detection, blood pressure, breathing rate, body weight, waist size, age.

In certain embodiments, individual rings may correspond to seconds, minutes, hours, days, months, years, or any other discrete bins or increments of time. In certain embodiments, the inner rings may represent more recent time increments and the outer rings may represent older time increments. In certain embodiments, a time point represented by a ring may be a snapshot of data at a particular time. In certain embodiments, a time point represented by a ring may correspond to an average or aggregate measurement of data spanning the range of time between the time associated with the time point and the time associated with an adjacent time point.

The appearance of a halo may be used to indicate variability in the underlying metrics. Each metric of interest is provided as a parameter for the halo. In certain embodiments, the same metric provides the data for multiple parameters. Whether a parameter affects a particular ring may be dependent on one or more attributes of the ring. An attribute may be a feature of the appearance of a ring, or may be metadata associated with a ring. An attribute of a ring may be set by a parameter. In certain embodiments, a parameter may be compared to a threshold value. In certain embodiments, a parameter may scale an attribute of a ring, or may be used to select between different attributes of a ring.

Figure 3:
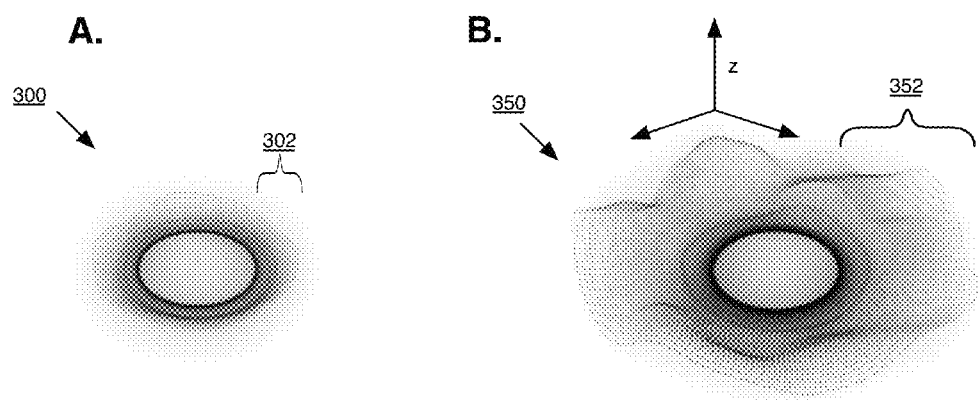
FIG. 3 shows two views of a halo (or alternatively, two halos), consistent with one embodiment of the invention.

In certain embodiments, a halo includes a size parameter. The size affects the width of the halo, as shown in width 108 of halo 100. In certain embodiments, the size scales the spacing between respective rings of the halo, such that a larger-sized halo is associated with more space between respective rings. In certain embodiments, an increase in size means that more rings are added to the halo. For example, as shown in FIG. 3, in certain embodiments, halo 300 and halo 350 are two different halos, where halo 350 has a greater size as compared to halo 300, because halo 350 contains more rings, leading to width 352 being greater than width 302. In certain embodiments, size scales both the spacing between the rings and the number of rings in the halo.

In certain embodiments, a halo represents a snapshot or summary of the status of a person, but respective rings are not associated with a particular time point. For example, the two halos in FIG. 3 may represent an individual's activity on two different days. Size may indicate the distance travelled each day, and thus for example halo 300 might represent a small halo where the individual didn't walk much, while halo 350 represents a larger halo for a day on which the individual went on a hike.

In certain embodiments, the halo includes a color parameter. The color may indicate the value of a metric within a range using a color spectrum, such as a range of RGB, HSL, HSV, or hexadecimal values. In certain embodiments the color may indicate a category or binary option. Individual rings may be colored separately, for instance where a ring represents a metric during an increment of time, or the color of an entire halo may represent the value of a metric. In certain embodiments, the entire halo may take on a color to indicate that the subject has passed a threshold—for example, halo 100 in FIG. 1 might be colored green to indicate that the individual has met her calories-burned goal for the day. In certain embodiments, halo 350 may be colored using a cooler color to indicate low intensity exercise and a warmer color as the individual's physical speed or gait increases, transitioning to higher intensity exercise (e.g., blue if the individual is currently walking, and red if the individual is currently running).

In certain embodiments, the halo includes a complexity parameter. The complexity parameter may scale the magnitude (e.g., amplitude or frequency) of distortions in one or more rings of the halo. In certain embodiments, the distortions may be periodic structures arranged along the path of one or more ring, such as sine waves or a sawtooth wave. A ring may be formed from a linear combination of multiple such waves.

For example, the path in three dimensions (x, y, z) of a ring having a sinusoidal distortion with amplitude a and frequency f is:

$$x=(R+a\cdot\sin(ft))\cdot\cos(t)+c_x$$

$$y=(R+a\cdot\sin(ft))\cdot\sin(t)+c_y$$

$$z=a\cdot\cos(ft))\cdot\cos(t)+c_z$$

where R is the radius of the ring, t is the angle ranging from 0 to $2\pi$, and ($c_x$, $c_y$, $c_z$) is the ring's center point.

For example, if complexity represents the intensity of an activity, a halo may include rings with increasing frequencies of distortion to indicate high intensity activity. For example, in halo 100, ring 102 is shown with a non-zero amplitude and frequency of distortion, whereas ring 104 has no distortion and thus no complexity, indicating that ring 102 could represent a time increment where the subject was active, and ring 104 could represent a time increment where the subject was not active.

Figure 4:
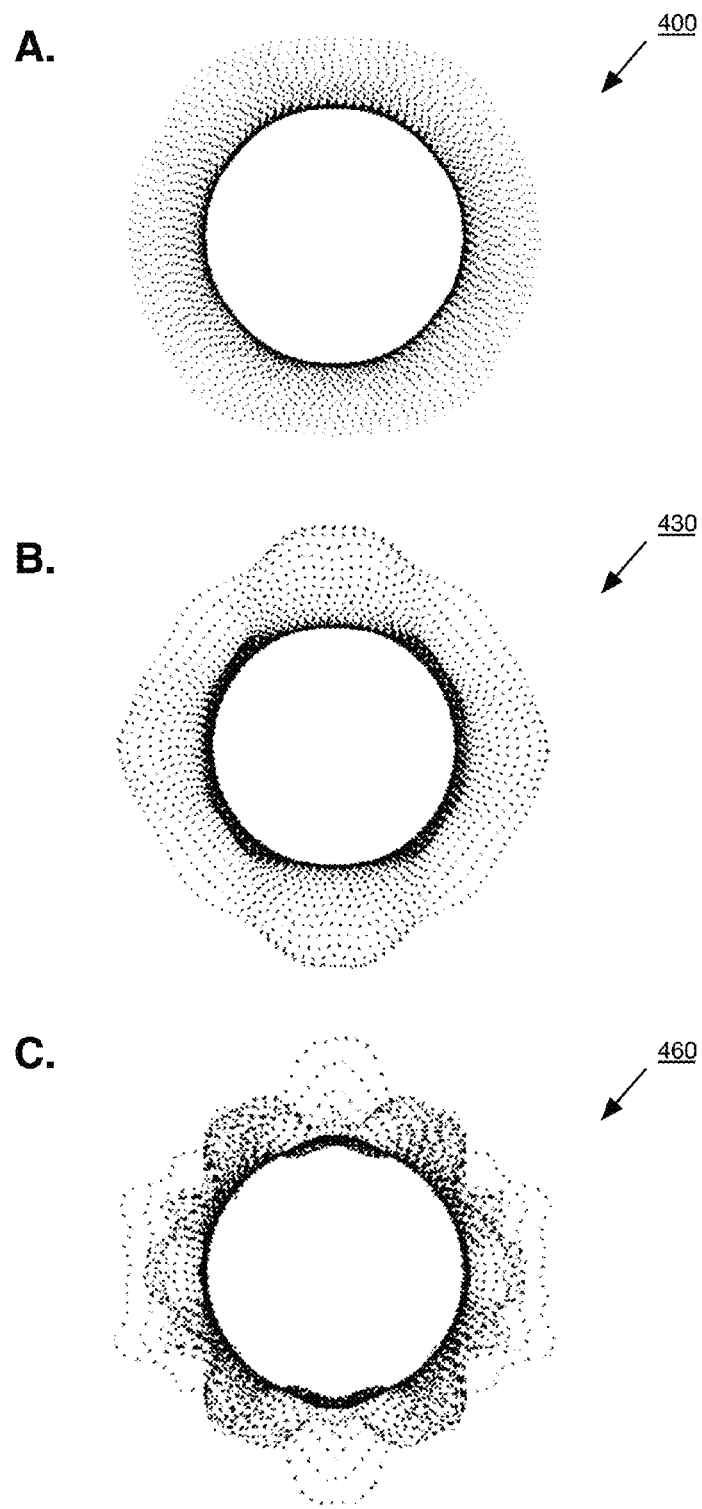
FIG. 4 shows three views of halos, consistent with one embodiment of the invention.

In another example, FIG. 4 shows three halos, each displaying increasing complexity. Specifically, each of halos 400, 430, and 460 is made up of rings having a sinusoidal distortion. The amplitude of the distortion increases from the lowest amplitude in the rings of halo 400 to the greatest amplitude in the rings of halo 460.

In certain embodiments, the halo includes a speed parameter. The speed parameter may scale the rate of movement of each ring within the halo. For example, in halo 100, ring 102 may transition between two or more shapes (for example, two shapes in which the amplitudes of distortion are reversed). Such a transition may occur through a smooth animation, with the rate of the transition scaled by the speed parameter. Individual rings may vibrate in place or oscillate around a fixed or moving point or path. In another example, in halo 350 rings may move in concert in the manner of a travelling wave. The rings may move individually or together within the x-y plane of the halo or out of the x-y plane along the z-axis. For example, an undulating movement along a radial line can be effected by setting the z-coordinate of each ring to follow the path of a sine wave moving along the radial line, where the rate of movement of the sine wave is scaled by the speed parameter. An undulating halo can be effected by modeling such a movement along all radial lines within the x-y plane.

In one example, the speed parameter for halo 350 may be set by the subject's heart rate. As the heart rate increases, the halo exhibits a faster undulation, providing a visual indication of the magnitude of the heart rate.

In certain embodiments, the speed parameter is responsive to a threshold value, and does not affect movement unless it passes a low or high threshold. In certain embodiments, the speed parameter scales movement of all rings equally. The speed parameter may also scale movement of different rings at different rates. Whether speed affects a particular ring may be dependent on one or more attributes of the ring. In certain embodiments, the the halo exhibits movement in the absence of a speed parameter or where the speed parameter is null or zero.

In certain embodiments, the halo includes a brightness parameter. The brightness parameter may scale the opacity of respective rings.

For example, brightness may be set by the subject's sleep state, such that if the subject was sleeping, a ring has low opacity. Thus, for example, in a halo with time-associated rings such as halo 100, rings corresponding to a period of sleep would appear dim, and rings corresponding to a waking state would appear brighter, providing a quick overview of sleep patterns across a set period of time such as a 24-hour day.

Figure 2:
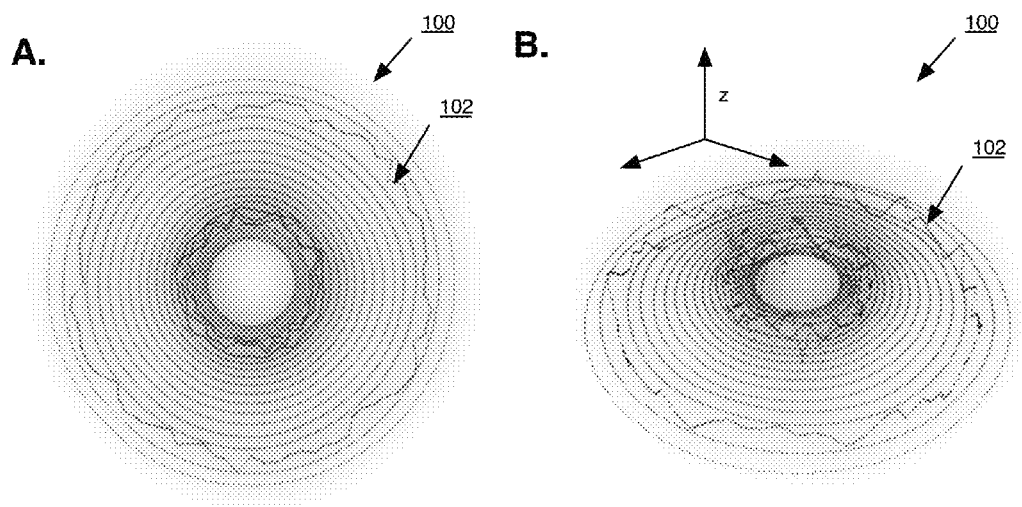
FIG. 2 shows two views of a halo, consistent with one embodiment of the invention.

In certain embodiments, the halo includes a height parameter. The height parameter may scale the magnitude of extension of distortions in respective rings outside of the plane of the halo. For example, as shown in FIGS. 2B and 3B, some halos may include rings in which portions of the rings extend outside of the x-y plane. In certain embodiments, off-plane extensions are temporary, as distortions in the ring oscillate above and below the x-y plane. Ring 102 in FIG. 2 provides one example of a ring in which portions of the ring—here, some of the distortions—extend above the x-y plane. In a halo such as halo 350, in which ripples in the rings may move in the manner of a travelling wave, the height parameter may scale the maximum height for the amplitude of the wave on the z-axis.

For example, the height parameter may be set by the subject's activity intensity, such that higher intensity activity will result in one or more rings extending further out of the x-y plane of the halo. In an example where the rings are in motion, the activity intensity may set the maximum extension for distortions in the rings. In some embodiments, a low or zero-level height will mean the corresponding ring will remain wholly within the plane of the halo.

Figure 5:
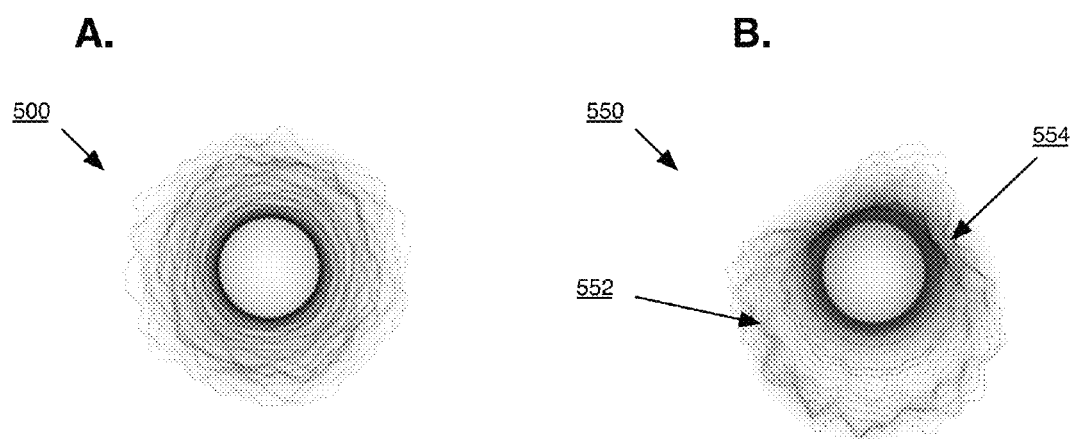
FIG. 5 shows two views of a halo (or alternatively, two halos), consistent with one embodiment of the invention.

In certain embodiments, the halo includes a movement type parameter. The movement type parameter may scale the asymmetry of movement of respective rings. For example, FIG. 5 shows snapshots of a halo 500 with symmetrical movement, and a halo 550 exhibiting asymmetrical movement. Asymmetrical movement of respective rings may be evaluated as a difference from rings having annular symmetry around the center point of the halo, such that as the halo moves, the movement is balanced around the center point of the halo. (For example, all of the halos shown in FIG. 4 have perfect annular symmetry around the center point of the halo, and in motion, the rings exhibit balanced movement.) In halo 550, the portions of rings falling into region 552 may appear to follow a different trajectory from the portions of rings falling into region 554.

In one example, the movement type parameter may provide a flag for abnormality. For example, where the movement type parameter corresponds to blood pressure, and while the blood pressure is in a healthy range, the halo may have a symmetrical appearance as with halo 500. If the blood pressure moves outside of the healthy range, the halo may take on an unbalanced, asymmetrical appearance as with halo 550.

In certain embodiments, the halo includes a rotation parameter. The rotation parameter may control the direction or speed of rotation of respective rings. For example, a halo representing a female game character may rotate in the clockwise direction, and a halo representing a male game character may rotate in the counterclockwise direction.

Figure 6:
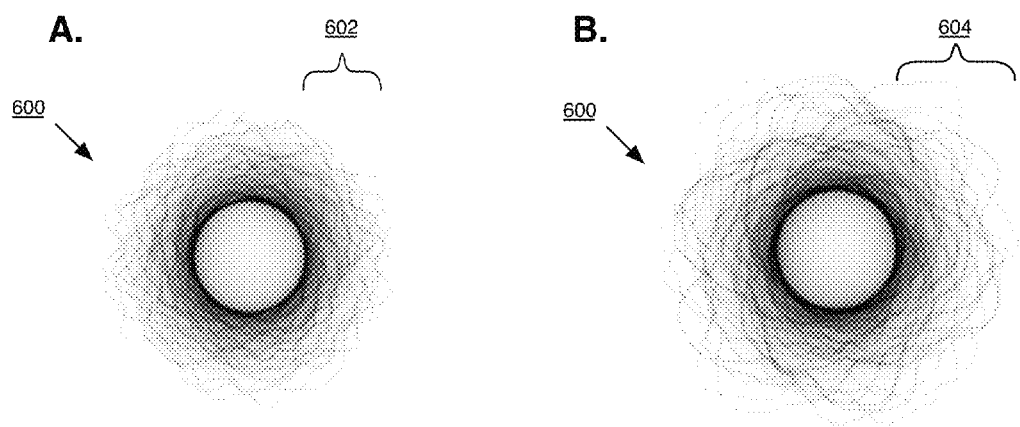
FIG. 6 shows two views of a halo, consistent with one embodiment of the invention.

In certain embodiments, the halo includes a pulsation parameter. The pulsation parameter may scale the frequency of a sequence of contraction and expansion of the width of the halo. FIG. 6 shows snapshots for a halo with a non-zero pulsation: the halo 600 transitions between a contracted appearance with a smaller width 602 and an expanded appearance with a wider width 604. In certain embodiments, only a subset of the rings may undergo expansion and contraction. In certain embodiments, the pulsation movement is accomplished by sequentially increasing and reducing the spacing between the rings.

For example, the pulsation parameter may correspond to the subject's heart rate. Accordingly, as the heart rate increases, the frequency of expansion and contraction increases as well. In one example, the pulsation frequency is the same as the heart rate. The pulsation may thus mimic a beating heart. In another example, the pulsation parameter corresponds to the subject's breathing rate, such that hyperventilation would be displayed as a rapidly pulsing halo.

Figure 7:
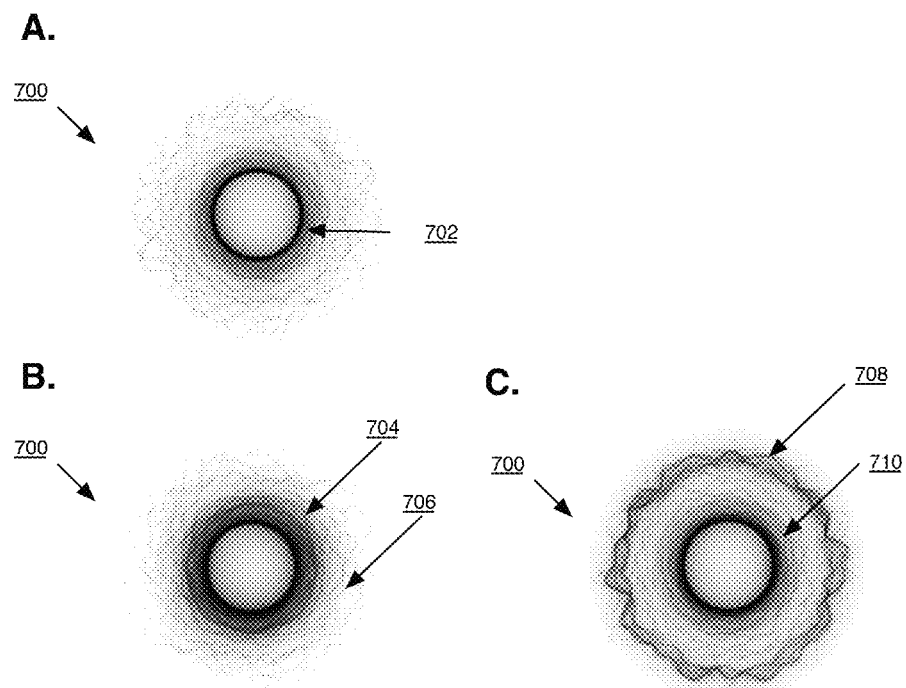
FIG. 7 shows three views of a halo, consistent with one embodiment of the invention.

In certain embodiments, the halo includes a radiation parameter. The radiation parameter may scale the magnitude or frequency of a sequential alteration in the appearance of a subset of the halo's rings, such that the sequence progresses from the center of the halo to the edge or the reverse. For example, FIG. 7 shows three snapshots of halo 700, in which the radiation sequence is causing the rings to become thicker and brightly colored relative to the normal ring appearance (e.g., the rings are highlighted). In FIG. 7A, all the rings appear normal, including rings 702. In FIG. 7B, rings at the center of the halo 704 are highlighted, while outer rings 706 maintain a normal appearance. In FIG. 7C, the rings at the center of the halo 710 appear normal again, the middle rings have been highlighted and then rendered normally, and now the outer rings 708 are highlighted. Thus this sequence of highlighting follows a repeating, radiating sequence.

In one example, the radiation parameter corresponds to a danger indicator, where if either of blood pressure or heart rate exceeds a respective threshold, the halo will exhibit a radiation sequence. In one example, the altered appearance for the sequence is the ring color becomes blue if due to blood pressure and red if due to heart rate, and becomes purple if both blood pressure and heart rate thresholds are exceeded (i.e., the colors corresponding to each attribute are combined). In another example, the frequency of the radiation sequence increases as the amount by which the threshold is exceeded increases.

In certain embodiments, the halo includes a glow parameter. The glow parameter may scale the magnitude or frequency of highlighting applied to the rings. For example, a halo exhibiting a glow may appear brighter than a halo without a glow, or the glow may cause the halo to appear to blink on and off.

In one example, the glow parameter may be set by the subject's sleep state, such that if the subject was sleeping, corresponding rings have a lower magnitude of highlighting applied. Thus, for example, in a halo with time-associated rings such as halo 100, rings corresponding to a period of sleep would appear dim, and rings corresponding to a waking state would appear highlighted, providing a quick overview of sleep patterns across a set period of time such as a 24-hour day.

In certain embodiments, the halo includes a line type parameter. The line type parameter may be used to select the line type for display of particular rings, where the line type may range between solid, dashed, and dotted lines. For example, a halo representing a female game character may be displayed with rings using solid lines, and a halo representing a male game character may be displayed with rings using dotted lines.

In certain embodiments, the halo includes a growth parameter. The growth parameter may scale a change in the number of rings displayed. For example, halo 300 and halo 350 may represent the same halo at different time points. If, for example, growth number is associated with step count during a subject's workout, additional rings may be added for every hundred steps during a workout. Thus halo 300 may represent aspects of the workout near the beginning of the workout, and halo 350 may represent aspects of the workout toward the end of the workout.

Figure 8:
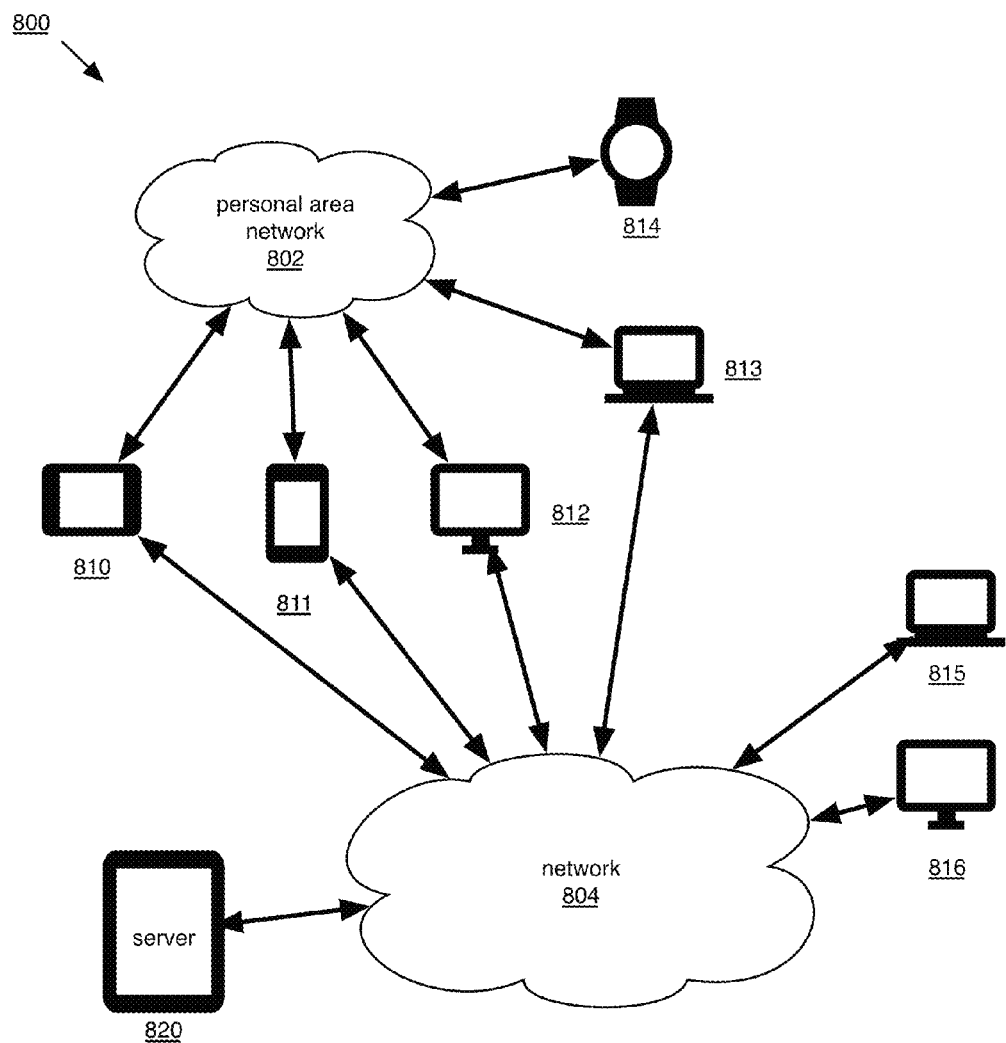
FIG. 8 is a block diagram showing exemplary data communication flows for an exemplary system, consistent with one embodiment of the invention.

FIG. 8 is a block diagram showing exemplary data communication flows for an exemplary system. In certain embodiments, the data sets or data streams to be transformed are received by one or more computing devices 810-814 associated by a personal area network 802. Computing devices may include mobile devices such as tablet 810, smart phone 811, and wearable computing device 814; other computing devices include laptop 813, desktop computer 812, and server 820. Personal area network 802 may include, for example, a piconet established using Bluetooth, or a wireless local area network (WLAN). In certain embodiments, the data to be transformed are received by server 820 or computing devices 815 and 816 via network 804. Network 804 may include a LAN, wired or wireless network, private or public network, or the internet.

Figure 9:
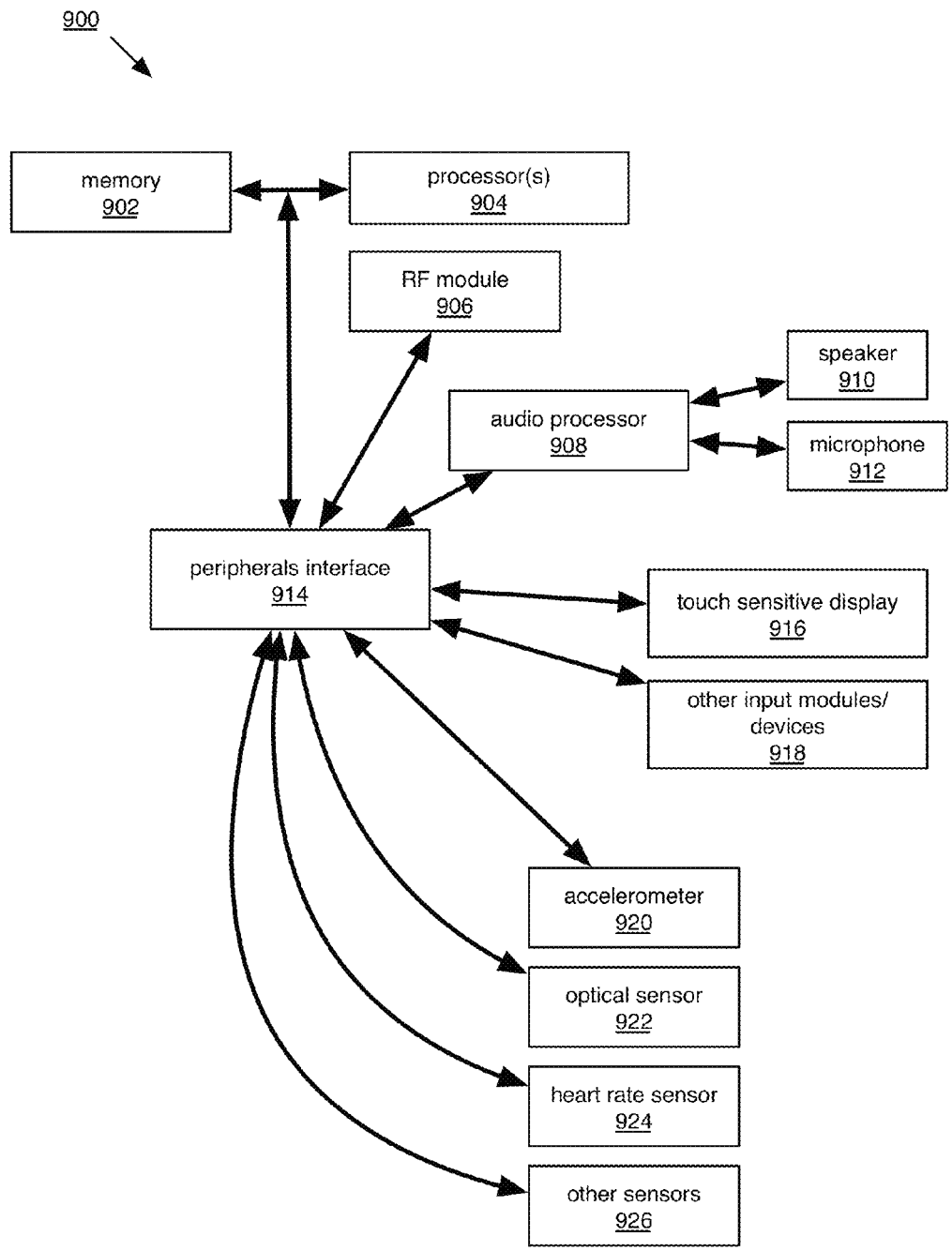
FIG. 9 is a block diagram showing an exemplary mobile computing device, consistent with one embodiment of the invention.

FIG. 9 is a block diagram showing an exemplary mobile computing device. The device 900 may have a memory 902 which may include one or more types of computer readable medium, such as RAM, optical storage devices, or flash memory. Memory 902 may store an operating system, applications, and communication procedures. Device 900 may include one or more data processors, image processors, or central processing units 904. Device 900 may include peripherals interface 914 coupled to RF module 906, audio processor 908, touch sensitive display 916, other input modules/devices 918, accelerometer 920, optical sensor 922, heart rate sensor 924, and other sensors 926.

RF module 906 may include a cellular radio, Bluetooth radio, NFC radio, WLAN radio, GPS receiver, and antennas used by each for communicating data over various networks.

Audio processor 908 may be coupled to a speaker 910 and microphone 912. Touch sensitive display 916 receives touch-based input. Other input modules or devices 918 may include, for example, a stylus, voice recognition via microphone 912, or an external keyboard.

Accelerometer 920 may be capable of detecting changes in orientation of the device, or movements due to the gait of a user. Optical sensor 922 may sense ambient light conditions, and acquire still images and video. Heart rate sensor 924 may estimate heart rate using, for example, a light source and photodetector. Other sensors 926 may include, for example, a blood alcohol sensor, a blood oxygen sensor, temperature sensor, skin conductance sensor, ballistocardiogram sensor, blood pressure sensor, blood glucose sensor, altimeter, gyroscope, microphone/noise detector.

Figure 10:
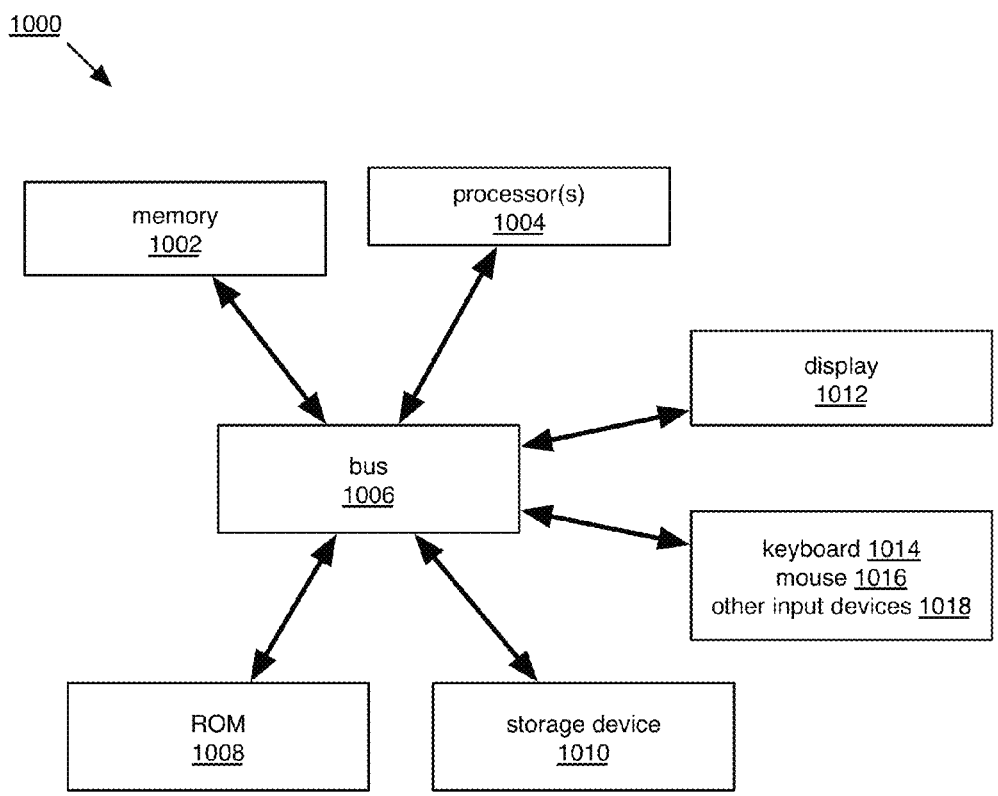
FIG. 10 is a block diagram showing an exemplary computing device, consistent with one embodiment of the invention.

FIG. 10 is a block diagram showing an exemplary computing device that is representative of computing systems discussed herein, such as computer 816 or server 820. Note, not all of the various computer systems have all of the features of system 1000. For example, systems may not include a display inasmuch as the display function may be provided by a client computer communicatively coupled to the computer system or a display function may be unnecessary.

System 1000 includes a bus 1006 or other communication mechanism for communicating information, and a processor 1004 coupled with the bus 1006 for processing information. Computer system 1000 also includes a main memory 1002, such as a random access memory or other dynamic storage device, coupled to the bus 1006 for storing information and instructions to be executed by processor 1004. Main memory 1002 also may be used for storing temporary variables or other intermediate information during execution of instructions to be executed by processor 1004.

System 1000 includes a read only memory 1008 or other static storage device coupled to the bus 1006 for storing static information and instructions for the processor 1004. A storage device 1010, which may be one or more of a hard disk, flash memory-based storage medium, magnetic tape or other magnetic storage medium, a compact disc (CD)-ROM, a digital versatile disk (DVD)-ROM, or other optical storage medium, or any other storage medium from which processor 1004 can read, is provided and coupled to the bus 1006 for storing information and instructions (e.g., operating systems, applications programs and the like).

Computer system 1000 may be coupled via the bus 1006 to a display 1012 for displaying information to a computer user. An input device such as keyboard 1014, mouse 1016, or other input devices 1018 may be coupled to the bus 1006 for communicating information and command selections to the processor 1004.

The processes referred to herein may be implemented by processor 1004 executing appropriate sequences of computer-readable instructions contained in main memory 1004. Such instructions may be read into main memory 1004 from another computer-readable medium, such as storage device 1010, and execution of the sequences of instructions contained in the main memory 1004 causes the processor 1004 to perform the associated actions. In alternative embodiments, hard-wired circuitry or firmware-controlled processing units (e.g., field programmable gate arrays) may be used in place of or in combination with processor 1004 and its associated computer software instructions to implement the invention. The computer-readable instructions may be rendered in any computer language including, without limitation, Objective C, C#, C/C++, Java, assembly language, markup languages (e.g., HTML, XML), and the like. In general, all of the aforementioned terms are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 1000 or similar electronic computing device, that manipulates and transforms data represented as physical (electronic) quantities within its registers and memories into other data similarly represented as physical quantities within its memories or registers or other such information storage, transmission or display devices.

Figure 11:
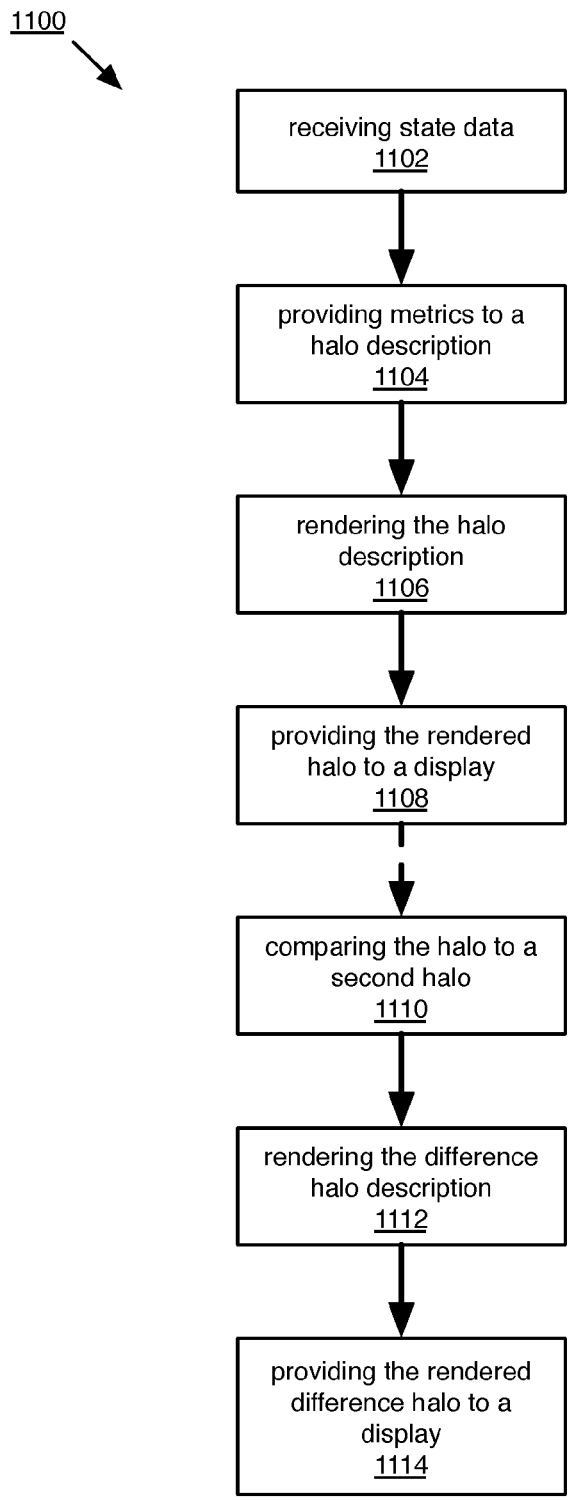
FIG. 11 is a flowchart representing exemplary methods for transforming complex state data into a halo-based visualization of the status of a subject and optionally comparing the halo to a second halo.

FIG. 11 is a flowchart representing exemplary methods for transforming complex state data into a halo-based visualization of the status of a subject and optionally comparing the halo to a second halo. In process 1100, a computing device receives state data (1102) providing information about the status of a subject. The subject may be, for example, a person in the middle of exercising, a person waking up in the morning, a video game character, or any other subject that may be associated with status data. In some embodiments, the subject may be wearing wearable device 814, with the data provided by sensors on device 814. In certain embodiments, wearable device 814 provides the state data to smart phone 811 or another device associated with personal area network 802. In certain embodiments, the data to be transformed are obtained from direct readings by a mobile device, such as smart phone 811 or wearable device 814. In certain embodiments, the data to be transformed are obtained from an online database. Some or all of the data may be directly entered by a user through the user interface of a computing device.

In some examples, the computing device may transform the status data into a set of metrics. The computing device provides metrics as parameters to a description of a halo (1104). A computing device renders the halo description (1106), and provides the rendered halo to a display (1108). In certain embodiments, the halo is rendered at a processor of a mobile device. In certain embodiments, the halo is rendered at a processor of a laptop or desktop computer such as computers 813, 812, or 816. In certain embodiments, the halo is rendered at a processor of server 820. In certain embodiments, the halo is displayed on the screen of wearable device 814, or the screen of another mobile device. In certain embodiments, the halo is displayed on the screen of laptop 813 or computer 812. In certain embodiments, the displayed halo may be manipulated and rotated using an input device such as a touchpad, mouse, or gestures on a touchscreen. In certain embodiments, the rendering step generates video that cannot be rotated or manipulated.

In some examples, two halos may be compared by comparing the underlying parameters for each halo (1110). For example, the system may calculate the difference between each corresponding parameter of the two halos (1112). Such "difference parameters" may be used to generate a third halo representing the distance between the two halos. For example, if the first halo has five sleep rings, and the second halo has eight sleep rings, the difference halo will include three sleep rings. In another example, the system may calculate the correlation between the two sets of parameters and provide a correlation score. The system may provide the rendered difference halo to a display (1114).

In one embodiment, a server may host halos corresponding to different users. The server may serve a website displaying the halos corresponding to different users. Users may login to the website to view the halo of another user, or view a "difference halo" providing a comparison between a halo corresponding to the user and a second halo corresponding to a different user.

In one example, two halos may be compared where one halo represents the current halo for a subject, and the second is based on past data for the subject, such that the comparison provides an overview of the improvement or progress made by the subject.

In another example, two halos may be compared where one halo represents the current halo for a subject, and the second is based on target data for the subject, such that the comparison indicates whether the subject has met a goal, or how much progress in which areas is needed in order to meet a goal.

In another example, two halos may be compared where one halo represents the current halo for a subject, and the second is based on a pathological or undesirable state. In this case, the comparison may indicate whether the subject meets or does not meet criteria for a pathological state, or how close the subject is to such a state.

In another example, two halos may be compared where one halo represents the current halo for a subject, and the second is based on data associated with a friend. In this example, a subject may determine how her status measures up to the friend's status.

The present system, its rendering, and presentation are the results of operations of data processing devices (e.g., processor-based computer systems) that may be interconnected with one another through one or more computer networks and/or networks of networks. The process descriptions and representations included herein are the means used by those skilled in the data processing and computer graphic arts to most effectively convey the substance of their work to others skilled in the art. The processes used to produce the present system may be regarded as one or more algorithms, where an algorithm is here, and generally, conceived to be a self-consistent sequence of steps leading to a desired result. These steps are those requiring physical manipulations of physical quantities. Usually, though not necessarily, these quantities may take the form of electrical or magnetic signals capable of being stored, transferred, combined, compared, displayed and otherwise manipulated. It proves convenient at times, principally for reasons of common usage, to refer to these signals as bits, values, elements, symbols, operations, messages, terms, numbers, or the like. It should be borne in mind, however, that all of these similar terms are to be associated with the appropriate physical quantities (e.g., in some instances heart rate or player performance information) and are merely convenient labels applied to these quantities.

In the present invention, the operations referred to are machine operations. Useful machines for performing the operations of the present invention include general-purpose digital computers or other similar devices (e.g., processor-based smart phones, tablets, etc.). In all cases, the reader is advised to keep in mind the distinction between the method operations of operating a computer and the method of computation to produce the user interface itself. The present invention relates to method steps for operating a computer, coupled to a series of networks, and processing electrical or other physical signals to generate other desired physical signals.

The present invention also relates to apparatus for performing these operations. The method/process steps presented herein when executed by a computer result in that computer becoming a special-purpose device for presentation of the subject user interface. Such devices may include any electronic device capable of performing the actions described above (using suitable programming) and, where applicable, processing the user performance information for display so as to properly convey the information in the form of the animated three-dimensional parametric shape. Examples of such devices include desktop computers, laptop computers, smart phones, tablet computers, computer game consoles, portable computer gaming consoles, media players, portable media players, other mobile devices, and the like, such as the computing devices of FIG. 8. In such devices, a processor may control the overall functions of the electronic device such as running applications and controlling peripherals. Such a processor may be any type of processor and may communicate with an RF receiver and RF transmitter to transmit and receive wireless signals (e.g., via an antenna) such as cellular, Bluetooth, Wi-Fi, WiLAN, or other communication signals. The processor may use short-term memory to store operating instructions and to help in the execution of the operating instructions (e.g., such as the temporary storage of calculations and the like). The processor may also use non-transitory storage to store and read instructions, files, and other data that requires long term, non-volatile storage.

This description includes the accompanying drawings, which form a part of this patent application. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using combination or permutation of those elements shown or described (or one or more aspects thereof), either with respect to a particular example (or one or more aspects thereof), or with respect to other examples (or one or more aspects thereof) shown or described herein.

What is claimed is:

1. A method for transforming complex state data into a visualization of the status of a subject at a range of time points, comprising:
   receiving, at a computing device, at least one data stream comprising state data for the subject, wherein the state data includes a plurality of metrics capturing information regarding the status of the subject at a series of time points;
   providing each metric in the plurality of metrics as a respective parameter to a description of a halo comprised of a plurality of rings, each respective ring corresponding to a time point, wherein at least two parameters are selected from the group consisting of:
      size, wherein size scales the spacing between respective rings,
      color, wherein color defines the color of respective rings,
      complexity, wherein complexity scales the magnitude and frequency of distortions in respective rings,
      speed, wherein speed scales the rate of movement of respective rings,
      brightness, wherein brightness scales the opacity of respective rings,
      height, wherein height scales the magnitude of extension of distortions in respective rings outside of the plane of the halo,
      movement type, wherein movement type scales the asymmetry of movement of respective rings,
      rotation, wherein the halo rotates clockwise or counterclockwise,
      pulsation, wherein pulsation scales the frequency of a sequence of contraction and expansion of the width of the halo,
      radiation, wherein radiation scales the magnitude or frequency of a sequential alteration of the appearance of a subset of the plurality of rings, such that the sequence progresses from the center of the halo to the edge or the reverse,
      glow, wherein glow scales the magnitude or frequency of highlighting applied to the plurality of rings, and
      line type, wherein line type selects between the display of respective rings using solid, dashed, and dotted lines;
   rendering the description of the halo at a processor, and providing the rendered description of the halo to a display.

2. The method of claim 1, wherein the at least one data stream includes heart rate data, accelerometer data, altimeter data, gyroscope data, or GPS data.

3. The method of claim 2, wherein one or more respective data stream of the at least one data stream is a real time data stream from a sensor on a wearable computing device.

4. The method of claim 1, wherein the at least one data stream includes data from an online database.

5. The method of claim 1, wherein the state data are transformed into the plurality of metrics.

6. The method of claim 1, wherein the plurality of metrics include heart rate, distance travelled, elevation climbed, step count, standing duration, activity duration, speed of movement, intensity of movement, calories burned, sleep cycle, hydration, electrical skin conductance, or tremor detection.

7. The method of claim 1, further comprising:
   comparing the halo to a second halo by calculating difference parameters representing the difference between corresponding parameters underlying the halo and the second halo;
   rendering a description of a third halo based on the difference parameters; and
   providing the rendered description of the third halo to a display.

8. The method of claim 7, wherein (1) the second halo is based on historical data associated with the subject, or (2) the second halo represents a target halo for the subject, or (3) the second halo represents an undesirable state, or (4) the second halo is based on data associated with a friend of the subject.

9. The method of claim 1, wherein the display is the touch screen display of a mobile device and the processor is located on a different mobile device.

10. The method of claim 1, wherein the display is the display of a computing device and the processor is located at a server.

11. A method for transforming complex state data into a visualization of the status of a subject, comprising:
   receiving, at a computing device, at least one data set comprising state data for the subject, wherein the at least one data set includes a plurality of metrics capturing information regarding the status of the subject;
providing each metric in the plurality of metrics as a respective parameter to a description of a halo comprised of a plurality of rings, wherein at least three parameters are selected from the group consisting of:
size, wherein size scales the width of the halo,
color, wherein color defines the color of the plurality of rings,
complexity, wherein complexity scales the magnitude and frequency of distortions in respective rings,
speed, wherein speed scales the rate of movement of respective rings,
brightness, wherein brightness scales the opacity of the plurality of rings,
height, wherein height scales the magnitude of extension of distortions in respective rings outside of the plane of the halo,
movement type, wherein movement type scales the asymmetry of movement of the plurality of rings,
rotation, wherein the halo rotates clockwise or counterclockwise,
pulsation, wherein pulsation scales the frequency of a sequence of contraction and expansion of the width of the halo,
radiation, wherein radiation scales the magnitude or frequency of a sequential alteration of the appearance of a subset of the plurality of rings, such that the sequence progresses from the center of the halo to the edge or the reverse,
glow, wherein glow scales the magnitude or frequency of highlighting applied to the plurality of rings,
line type, wherein line type selects between the display of respective rings using solid, dashed, and dotted lines, and
growth, wherein growth scales a change in the number of rings displayed;
rendering the description of the halo at a processor, and
providing the rendered description of the halo to a display.

12. The method of claim 11, wherein the at least one data set includes heart rate data, accelerometer data, altimeter data, gyroscope data, or GPS data.

13. The method of claim 12, wherein one or more respective data set of the at least one data set is a real time data stream from a sensor on a wearable computing device.

14. The method of claim 11, wherein the at least one data set includes data from an online database.

15. The method of claim 11, wherein the state data are transformed into the plurality of metrics.

16. The method of claim 11, wherein the plurality of metrics include heart rate, distance travelled, elevation climbed, step count, standing duration, activity duration, speed of movement, intensity of movement, calories burned, sleep cycle, hydration, electrical skin conductance, or tremor detection.

17. The method of claim 16, wherein (1) the second halo is based on historical data associated with the subject, or (2) the second halo represents a target halo for the subject, or (3) the second halo represents an undesirable state, or (4) the second halo is based on data associated with a friend of the subject.

18. The method of claim 11, further comprising:
comparing the halo to a second halo by calculating difference parameters representing the difference between corresponding parameters underlying the halo and the second halo;
rendering a description of a third halo based on the difference parameters; and
providing the rendered description of the third halo to a display.

19. The method of claim 11, wherein the display is the touch screen display of a mobile device and the processor is located on a different mobile device.

20. The method of claim 11, wherein the display is the display of a computing device and the processor is located at a server.

* * * * *